(12) United States Patent
Carcone et al.

(10) Patent No.: US 9,067,868 B2
(45) Date of Patent: Jun. 30, 2015

US009067868B2

(54) CHEMICAL PROCESS FOR OPENING RING COMPOUNDS

(75) Inventors: Luca Carcone, Cervaro (IT); Domenico Magrone, Verona (IT); Giuseppe Barreca, Montevecchia (IT); Marcello Rasparini, Cura Carpignano (IT); Huang Liming, Haiyou Town (CN)

(73) Assignee: Chemo Iberica, S.A., Barcelona (ES)

( * ) Notice: Subject to any disclaimer, the term of this patent is extended or adjusted under 35 U.S.C. 154(b) by 0 days.

(21) Appl. No.: 14/131,973

(22) PCT Filed: Jul. 25, 2012

(86) PCT No.: PCT/EP2012/064607
§ 371 (c)(1),
(2), (4) Date: Mar. 27, 2014

(87) PCT Pub. No.: WO2013/014191
PCT Pub. Date: Jan. 31, 2013

(65) Prior Publication Data
US 2014/0213821 A1    Jul. 31, 2014

(30) Foreign Application Priority Data
Jul. 28, 2011  (EP) .................................. 11382261

(51) Int. Cl.
*C07C 231/02* (2006.01)
*C07C 231/14* (2006.01)
*C07C 231/12* (2006.01)

(52) U.S. Cl.
CPC ............. *C07C 231/02* (2013.01); *C07C 231/14* (2013.01); *C07C 231/12* (2013.01)

(58) Field of Classification Search
CPC .... C07C 231/02; C07C 231/12; C07C 231/14
USPC .................................................... 564/134, 157
See application file for complete search history.

(56) References Cited

U.S. PATENT DOCUMENTS 2,752,334 A     6/1956  Walton et al.
2011/0137047 A1*  6/2011  Soukup ........................ 548/517

FOREIGN PATENT DOCUMENTS

JP         5221946       8/1993
JP         6135914       5/1994
WO      WO2011/019789   2/2011

OTHER PUBLICATIONS

PCT Search Report and Written Opinion for PCT/EP2012/064607, completed Oct. 5, 2012.
Foley, Megan A., et al., "Amide Bond Formation via Reversible, Carboxylic Acid-Promoted Lactone Aminolysis", 2010, American Chemical Society, vol. 14, No. 5, pp. 1177-1181.

* cited by examiner

*Primary Examiner* — Shailendra Kumar
(74) *Attorney, Agent, or Firm* — Barnes & Thornburg LLP

(57) ABSTRACT

It is described a process for the opening of lactone or lactam rings useful in the synthesis of pharmaceutically active compounds and the intermediates thereof, particularly Aliskiren. It has found that by selecting a type of solvent it is possible to obtain excellent yields and high optical and chemical purity of the isolated products.

19 Claims, No Drawings

CHEMICAL PROCESS FOR OPENING RING COMPOUNDS

CROSS-REFERENCE TO RELATED APPLICATIONS

This application is a national stage entry under 35 U.S.C. §371(b) of International Application No. PCT/EP2012/064607, filed Jul. 25, 2012, which claims the benefit of European Patent Application Serial No. 11382261.3, filed Jul. 28, 2011, the disclosures of which are hereby incorporated herein by reference.

FIELD OF THE INVENTION

The present invention relates to a process for the opening of lactone or lactam rings useful in the synthesis of pharmaceutically active compounds and the intermediates thereof, particularly Aliskiren.

BACKGROUND OF THE INVENTION

Renin is a proteolytic enzyme, belonging to the class of the hydrolases secreted by the juxtaglomerular apparatus cells in the kidneys, which, if activated, passes to blood, where it induces the hydrolysis of angiotensin and the following release of the decapeptide angiotensin I, which is hydrolyzed in the lungs, in the kidneys and in many other organs to provide the octapeptide angiotensin II.

This peptide increases blood pressure both directly, inducing arterial vasoconstriction, and indirectly, causing the release from adrenergic glands of the aldosterone, a hormone which raises the retention of sodium ions, inducing an increase of the extracellular fluid volumes.

Renin inhibitors reduce the formation of angiotensin I and consequently of angiotensin II. The reduced concentration of these peptides is the main reason for the hypotensive effect of these inhibitors, making them useful in the prevention and the treatment of hypertension, of heart failure, glaucoma, myocardial infarction and renal failure.

Aliskiren is the first of a new class of orally available potent renin inhibitors approved by FDA and EMEA.

In particular, its hemifumarate salt is registered by Novartis with the commercial name of Tekturna®. Chemically it is defined as (2S,4S,5S,7S)-5-amino-N-(3-amino-2,2-dimethyl-3-oxopropyl)-4-hydroxy-2-isopropyl-7-(4-methoxy-3-(3-methoxypropoxy)benzyl)-8-methylnonanamide hemifumarate. Aliskiren (1) is schematized in the picture below:

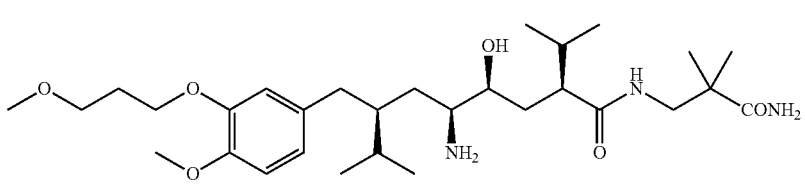

European patent EP 0678503 B1 claims Aliskiren (specifically its hemifumarate salt) and the method to produce it. This process involves the opening of the lactone ring in compound (I) by treatment with an amine (4) in presence of triethylamine (TEA) and 2-hydroxypyridine, as represented in the scheme below:

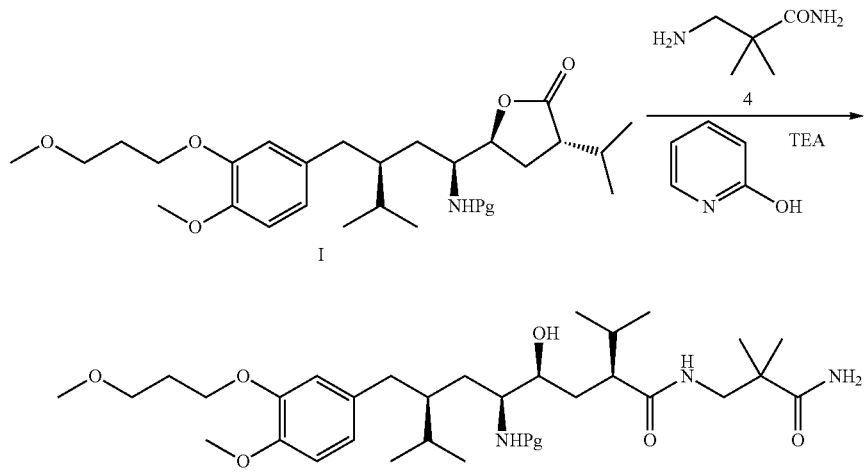

Similar processes are described in international patent applications WO 02/08172 A1 and WO 02/02508 A1, assigned to Speedel Pharma, in patent application US 2010/0124550 A1 assigned to Auspex Pharmaceuticals, or in international patent application WO 2010/024772 A1 assigned to Medivir Ab.

Lactone ring opening can be achieved by treatment with the amine (4) using a solvent and a base such as triethylamine or dimethylaminopyridine, as described in international application WO 2007/039183 A1 assigned to Novartis.

An alternative process is described in "A stereocontrolled synthesis of 2R-benzyl-5S-tert-butoxycarbonylamino-4R-(tert-butyldimethylsilanyloxy)-6-phenyl-hexanoic acid"; A. Nadin et al.: *Tetrahedron* (2001), 57(9), 1861-1864, where the lactone ring is hydrolyzed to the corresponding hydroxy acid, followed by protection of the alcohol and formation of the amide bond using a coupling agent.

A direct aminolysis process is described in "Formal Total Synthesis of the Potent Renin Inhibitor Aliskiren: Application of a SmI$_2$-Promoted Acyl-like Radical Coupling" K. B. Lindsay et al.: *Journal of Organic Chemistry* (2006), 71(13), 4766-4767. According to the process described therein, the lactone ring in compound (I) is treated with the amine (4) in presence of Al(CH$_3$)$_3$.

Another synthetic method to open a lactone ring, described in international application WO 03/103653 A1 assigned to Elan Pharmaceuticals, entails the reaction with the amine (4) in the presence of a carboxylic acid, specifically acetic acid.

However, all the process cited above provide the desired amide with extremely low yields and in some cases involve the use of reagents not easily handled on industrial scale.

Improved processes of direct aminolysis are described in "A convergent synthesis approach towards CGP60536B, a non-peptide orally potent renin inhibitor, via an enantiomerically pure ketolactone intermediate", H. Rüeger et al.: *Tetrahedron Letters* (2000), 40(51), 10085-10089, in which compound (I) is reacted under solvent free conditions with the amine (4), triethylamine and 2-hydroxypyridine; or in European patent EP 1789377 B1, where the same reaction is conducted using a solvent, particularly methyl-tert-butylether. These two processes provide the desired amide in extremely low yields.

A further improvement in the synthetic process of lactone ring opening is reported in "Amide Bond Formation via Reversible, Carboxylic Acid-Promoted Lactone Aminolysis", M. A. Foley et al.: *Organic Process Research & Development* (2010), 14(5), 1177-1181, or in international patent application WO 2011/019789 A1 (assigned to Novartis), where the best yields for the aminolysis reaction are obtained treating the lactone (I) with an excess of amine (4) under solvent free conditions and in the presence of 2-ethylhexanoic acid as catalyst.

These two synthetic processes, which are indeed improvements with respect to the prior art, are affected by very low yields which could be enhanced to acceptable levels (HPLC measured conversion of 90%) only using enormous excesses of the amine (4) (up to 100 equivalents).

Furthermore the use of solvent free conditions can be problematic on an industrial scale.

It is thus an object of the present invention to provide an industrial process for the production of active ingredients and the intermediates thereof, particularly Aliskiren, which entails an opening of lactone or lactam ring as a key step, leading to an improved yield compared to the processes of the prior art.

SUMMARY OF THE INVENTION

This and other purposes are achieved within the present invention, which regards an aminolysis process of lactone or lactam rings by treatment with an amine of general formula RR$^{10}$NH, in presence of a catalyst and optionally of a cocatalyst, in a solvent in which the lactone or the lactam ring-containing compound is soluble and the amide, product of the reaction, is insoluble in the reaction conditions.

The inventors have surprisingly found that by selecting a solvent with the properties listed above it is possible to obtain excellent yields and high optical and chemical purity of the isolated products.

Particularly, the present invention is directed to the preparation of a compound (III) by treatment of a lactone or lactam ring-containing compound (II) with an amine of general formula RR$^{10}$NH, in presence of a catalyst and in a solvent where the product is insoluble in the reaction conditions, as depicted in the scheme below:

in which the substituents have the following meanings:
- R is hydrogen or a group selected among a linear or branched C1-C6 alkyl, preferably substituted, or an aryl (C1-C6) alkyl;
- R$^1$, R$^7$, R$^8$ and R$^9$ are, independently from each other, hydrogen, OH, OPg or a group selected among alkoxy C1-C10 or OR$^5$OR$^{11}$;
- R$^2$ is a group selected among a linear or branched C1-C6 alkyl or a linear or branched C1-C6 alkenyl;
- R$^3$ is selected among NH$_2$, NHPg, N(Pg)$_2$, N$_3$, halogen, NO$_2$, OH, OLg;
- R$^4$ is selected among O, NH, NPg;
- R$^5$ is a group selected among a linear or branched C1-C6 alkyl or a linear or branched C1-C6 alkenyl;
- R$^6$ is a group selected among a linear or branched C1-C6 alkyl or a linear or branched C1-C6 alkenyl;
- R$^{10}$ is hydrogen or a group selected among a linear or branched C1-C6 alkyl, preferably substituted, or an aryl (C1-C6) alkyl;
- R$^{11}$ is a group selected among a linear or branched C1-C6 alkyl or a linear or branched C1-C6 alkenyl;
- Pg is one of the protecting groups of the hydroxy function or of the amine function known in the field; and
- Lg is one of the leaving groups known by the person skilled in the art; with the condition that R and R$^{10}$ cannot be simultaneously hydrogen.

With the definition "aryl (C1-C6) alkyl", as used in the text and in the claims, it is intended a linear or branched C1-C6 alkyl substituted with an aryl group.

Optionally compound (III), obtained as a product of the aminolysis reaction, can be converted into a renin inhibitor by removing the protecting groups possibly present in the compound.

A further aspect of the present invention is a process for the preparation of Aliskiren or its pharmaceutically acceptable salts or one of the intermediates useful for its synthesis, by treating a lactone or lactam ring-containing compound (II) in the conditions described above and optionally converting the intermediate so obtained in Aliskiren or its salt.

A favorite object of this invention is a process to prepare the hemifumarate salt to of (2S,4S,5S,7S)-5-amino-N-(3-amino-2,2-dimethyl-3-oxopropyl)-4-hydroxy-2-isopropyl-7-(4-methoxy-3-(3-methoxypropoxy)benzyl)-8-methylnonanamide, which comprises reacting a tert-butyl or a benzyl ((1S,3S)-1-((2S,4S)-4-isopropyl-5-oxotetrahydrofuran-2-yl)-3-(4-methoxy-3-(3-methoxypropoxy)benzyl)-4-methylpentyl)carbamate with 3-amino-2,2-dimethylpropanamide in an appropriate solvent in the presence of a catalyst and optionally converting the so obtained ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate in the hemifumarate salt of Aliskiren by removing the present protecting groups and subsequently by reacting with fumaric acid.

DETAILED DESCRIPTION OF THE INVENTION

The synthetic process object of this invention comprises the aminolysis of a lactone or lactam ring-containing compound (II) (in the case of a lactam ring, optionally protected), solubilized in a suitable solvent, by treatment with a primary or secondary amine of general formula $RR^{10}NH$ in presence of a catalyst.

Optionally the so obtained compound (III) can be deprotected by the present protecting groups and subsequently converted into one of its pharmaceutically acceptable salts, by treatment for example with an inorganic acid, to provide preferably its hydrocloride or its hydrobromide, or by treatment with an organic acid to produce for example its malic, maleic or succinic salt, preferably its hemifumarate salt.

Lactone or lactam ring-containing compounds are understood as those of general formula (II) which contain at least one of these rings, but they could also contain them simultaneously.

The term catalyst refers to any compounds which can promote the lactone or to lactam ring opening to provide the product (III) under the reaction conditions described above.

Furthermore all compounds cited in the present description that admit enantiomer or diastereoisomer form may be present as racemic mixture, enantio- or diastereo-enriched mixture or in the form of isolated diastereoisomers or enantiomers.

The aminolysis of the lactone or lactam containing compound (II) is schematized below:

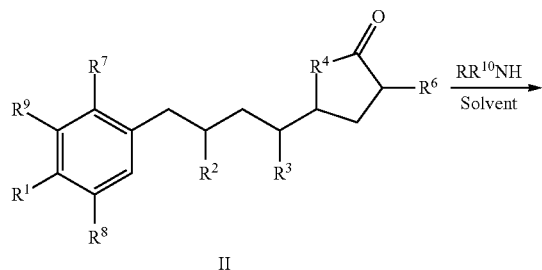

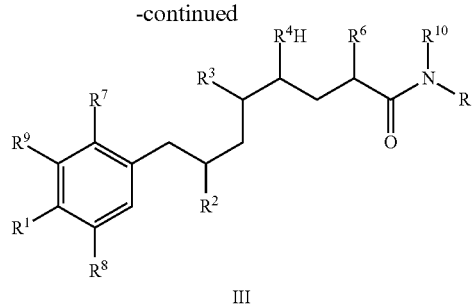

wherein the substituents have the meanings previously given.

The aminolysis of the lactam or lactone ring-containing compound (II) is carried out by treatment with an amine of general formula $RR^{10}NH$, in a suitable solvent with a catalyst, which could be a Brønsted acid, preferably weak, optionally (when the catalyst used is an aromatic heterocyclic compound) in the presence of a cocatalyst such as, for example, a tertiary amine (preferably triethylamine), at a temperature in the range comprised between 50-100° C., preferably between 60 and 85° C.

Possible catalysts are acids, which can be carboxylic, preferably monocarboxylic, of general formula $R^{12}CO_2H$, where $R^{12}$ is for example a linear or branched alkyl, a cycloalkyl, a linear or branched alkenyl, an aryl, or an arylalkyl; preferred is 2-ethylhexanoic acid.

An alternative class of acids that can be used as catalysts in the present invention are organosulfur compounds of general formula $R^{12}SO_3H$ in which to the possible meanings of $R^{12}$ are the same described above (for example camphorsulfonic acid).

Furthermore possible catalysts useful for the purpose are aromatic heterocyclic compounds, preferably monocyclic, containing at least one hydroxyl function (OH) optionally in equilibrium with its keto form, optionally and variably substituted, such as, for example, thiobarbituric acid or preferably 2-hydroxypyridine.

The amount of catalyst used in the reaction is comprised between 0.5 and 1.5 equivalents compared to the molar quantity of lactone or lactam ring-containing compound (II) used, preferably 0.5 equivalents in the case of a monocarboxylic acid (for example 2-ethylhexanoic acid) or 1 equivalent when an aromatic heterocyclic compound is used, such as, for example, 2-hydroxypyridine.

Cocatalysts useful for the aim (when the catalyst used is an aromatic heterocyclic compound), are organic bases, as amines, preferably tertiary, in which the substituent linked to the nitrogen atom are selected among a linear or branched C1-C7 alkyl, a linear or branched C1-C7 alkenyl, a C3-C8 cycloalkyl, an aryl, a heteroaryl, a heteroarylalkyl, such as, for example, triethylamine, 1,8-Diazabicyclo[5.4.0]undec-7-ene (DBU), ethyldiisopropylamine, pyridine, N-methylmorpholine or 4-dimethylaminopyridine (DMAP).

The amount of cocatalyst used in the reaction is comprised between 0.5 and 1.5 equivalents compared to the molar quantity of lactone or lactam ring-containing compound (II) used, preferably 1.2 equivalents.

Solvents useful for the present invention are those in which the product (III), but not the lactone or lactam ring-containing compound (II), is insoluble, in the temperature range in which the reaction is carried out. Those solvents could be, for example, aprotic apolar solvents, preferably hydrocarbons such as alkanes (C5-C10 linear or branched), cycloalkanes (preferably C5-C10, optionally branched), ethers, preferably dialkyl ethers (C5-C10 linear or branched); particularly preferred solvents are heptane, isopropyl ether, and cyclohexane.

The aminolysis process is the reaction of the lactone or lactam ring-containing compound (II) with a primary or a secondary amine of general formula $RR^{10}NH$, in which R and $R^{10}$ have the meanings given above. Possible substitutions in the R and $R^{10}$ substituents can comprise a cyano group, a free carboxylic group, an ester (with a linear or branched C1-C6 alkyl, a linear or branched C1-C6 alkenyl, a C3-C8 cycloalkyl, an aryl, an arylalkyl), an amide (N-unsubstituted, N-mono- or N-disubstituted for example with a linear or branched C1-C6 alkyl, a linear or branched C1-C6 alkenyl, a C3-C8 cycloalkyl, an aryl, an arylalkyl), an aldehyde or an acetal. Preferably when the C1-C6 alkyl is substituted with an amide this is a primary amide of formula $-(CO)NH_2$.

The preferred compound for the purposes of this invention is 3-amino-2,2-dimethylpropanamide.

The amount of amine $RR^{10}NH$ used is comprised in a range between 1.5 and 3.5 equivalents compared to the molar quantity of the lactone or lactam ring-containing compound (II), preferably variable among 2 and 3 equivalents when an acid or an aromatic heterocyclic compound is used as catalyst (such as 2-ethylhexanoic acid or 2-hydroxypyridine).

In general, the aminolysis reaction, object of this invention, occurs with different rates depending on the conditions and on the reagents used.

Optionally product (III), obtained by aminolysis of the lactone or lactam ring-containing compound (II), can be converted into a renin inhibitor by reduction (for example of an azide) or by removal of the optional protecting groups present in the compound.

The protection or the removal of these protecting groups can be carried out according to one of the methods known in the field, such as, for example, the ones reported in the Theodora W. Green, *Protective Groups in Organic Synthesis*, John Wiley & Sons (1999).

Preferred object of this invention is an aminolysis process of compounds (V) where one, two or preferably all the stereocenters have the configuration depicted in the picture below:

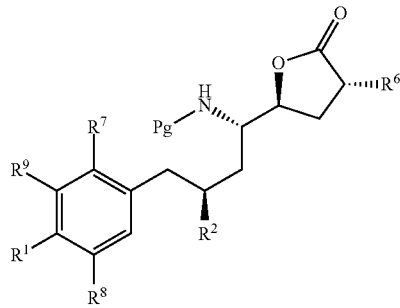

The meanings of the substituents are the same given above for compound (III).

Preferably the protecting groups (Pg) usable in this invention are those that, linked to the $-NH$ group, form a carbamate such as, for example, an alkoxycarbonyl (preferably tert-butoxycarbonyl, abbreviated Boc) variably and optionally substituted (for example with a linear or branched alkyl, a linear or branched alkoxy, a nitro group or a halide), an arylalkoxycarbonyl (preferably benzyloxy carbonyl, abbreviated Cbz or Z), optionally and variably substituted (for example with a linear or branched alkyl, a linear or branched alkoxy, a nitro group or a halide), a C2-C20 alkylthiocarbonyl, (preferably dodecylthiocarbonyl), an arylthiocarbonyl, or an arylalkylthiocarbonyl.

Example of possible protecting groups are $p-NO_2$-benzyloxycarbonyl, diphenylmethoxy carbonyl, allyloxycarbonyl or 2,2,2-trichloroethoxy carbonyl.

The invention will be further illustrated by means of the following examples.

Example 1

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH_2)_3OCH_3$, $R=CH_2C(CH_3)_2CONH_2$.

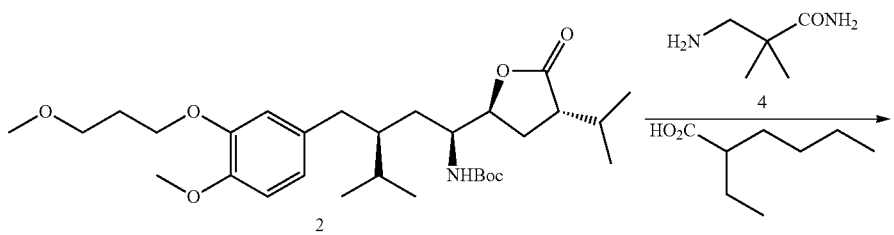

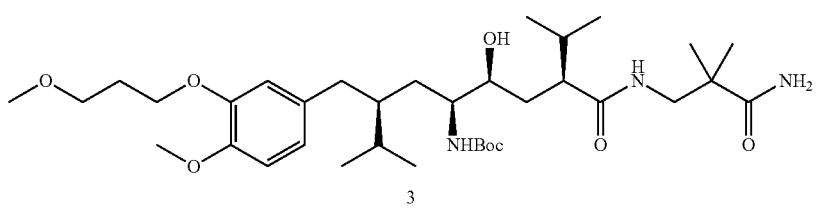

2-Ethylhexanoic acid (0.13 g, 0.90 mmol) is added to a stirred suspension of the lactone (2) (0.95 g, 1.77 mmol) and the amine (4) (0.52 g, 4.47 mmol) in heptane (10.0 mL).

The mixture is warmed to 60° C. and maintained under magnetic stirring until a conversion (by HPLC) higher than 95% is achieved (which takes about 40 hours).

After cooling to room temperature water (10.0 mL) is added with stirring to obtain a suspension, which can be easily filtered, and then washed with water and heptane.

The residue can be further purified crystallizing from isopropyl acetate obtaining (3) (1.08 g, 94%) as a white solid.

Example 2

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (10.0 mL) is added with stirring to obtain a suspension, which can be easily filtered, and then washed with water and isopropyl ether.

The residue can be further purified crystallizing from isopropyl acetate obtaining (3) (1.04 g, 90%) as a white solid.

Example 3

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

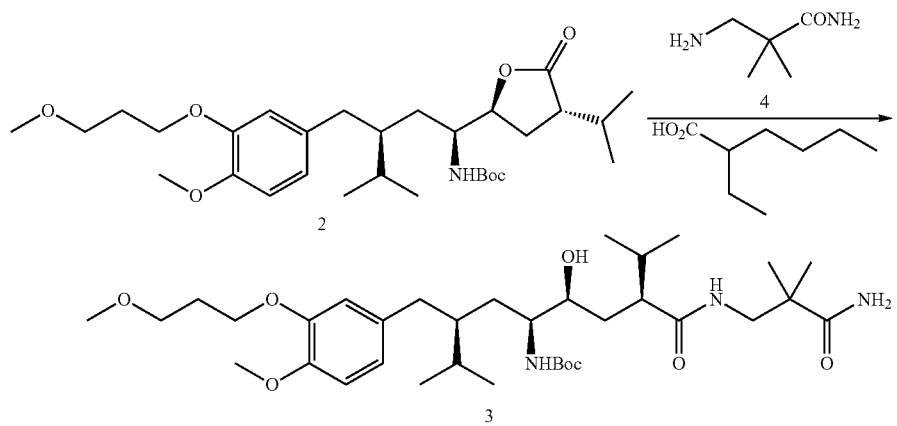

2-Ethylhexanoic acid (0.13 g, 0.90 mmol) is added to a stirred suspension of the lactone (2) (0.95 g, 1.77 mmol) and the amine (4) (0.52 g, 4.47 mmol) in isopropyl ether (10.0 mL).

The mixture is warmed to 60° C. and maintained under magnetic stirring until a conversion (by HPLC) higher than 95% is achieved.

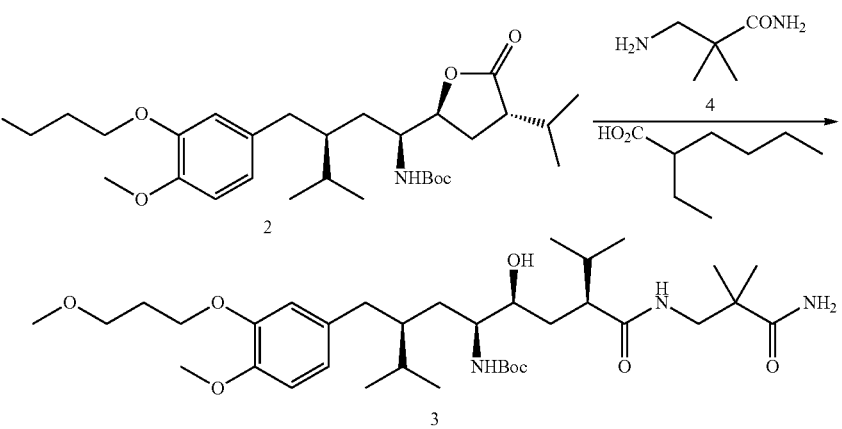

2-Ethylhexanoic acid (0.13 g, 0.90 mmol) is added to a stirred suspension of the lactone (2) (0.95 g, 1.77 mmol) and the amine (4) (0.52 g, 4.47 mmol) in cyclohexane (10.0 mL).

The mixture is warmed to 60° C. and maintained under magnetic stirring until a conversion (by HPLC) higher than 95% is achieved.

After cooling to room temperature water (10.0 mL) is added with stirring to obtain a suspension, which can be easily filtered, and then washed with water and cyclohexane.

The residue can be further purified crystallizing from iso-propyl acetate obtaining (3) (1.04 g, 90%) as a white solid.

Example 4

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (20.0 mL) is added with stirring to obtain a suspension, which can be easily filtered, and then washed with water and heptane.

The residue can be further purified crystallizing from iso-propyl acetate obtaining (3) (2.25 g, 94%) as a white solid.

Example 5

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

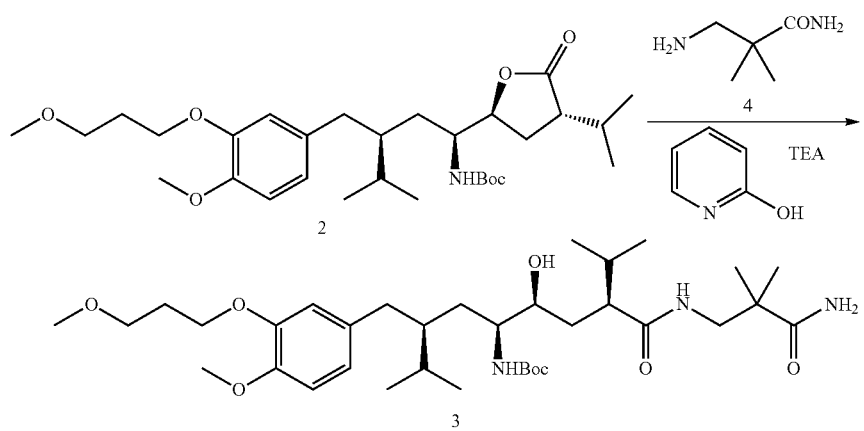

2-hydroxypiridine (0.35 g, 3.68 mmol) and triethylamine (0.45 g, 4.45 mmol) are added to a stirred suspension of the lactone (2) (2.00 g, 3.73 mmol) and the amine (4) (1.30 g, 11.19 mmol) in heptane (20.0 mL).

The mixture is warmed to 60° C. and maintained under magnetic stirring until a conversion (by HPLC) higher than 95% is achieved.

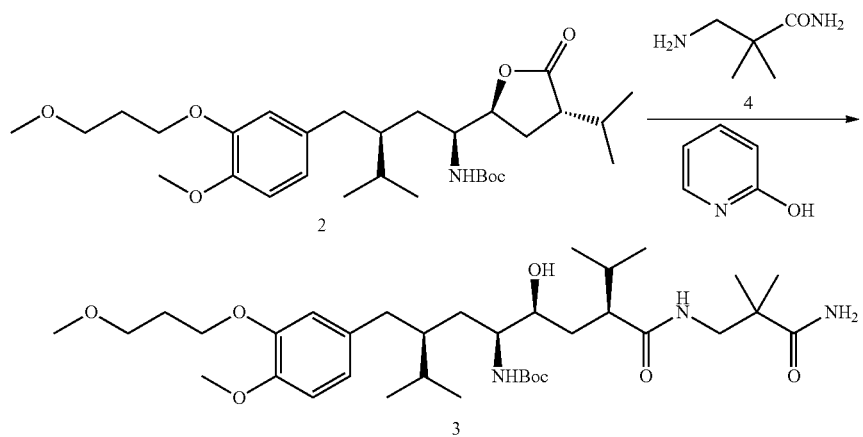

2-hydroxypiridine (0.35 g, 3.68 mmol) is added to a stirred suspension of the lactone(2) (2.00 g, 3.73 mmol) and the amine (4) (1.30 g, 11.19 mmol) in heptane (20.0 mL).

The mixture is warmed to 60° C. and maintained under magnetic stirring until a conversion (by HPLC) higher than 95% is achieved.

After cooling to room temperature water (20.0 mL) is added with stirring to obtain a suspension, which can be easily filtered, and then washed with water and heptane.

The residue can be further purified crystallizing from iso-propyl acetate obtaining (3) (2.22 g, 91%) as a white solid.

Example 6

Not Part of the Invention

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (20.0 mL) is added with stirring to obtain a suspension, which can be easily filtered, and then washed with water and heptane.

A mixture (2):(3)=80:20 is obtained in the solid.

Example 7

Not Part of the Invention

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

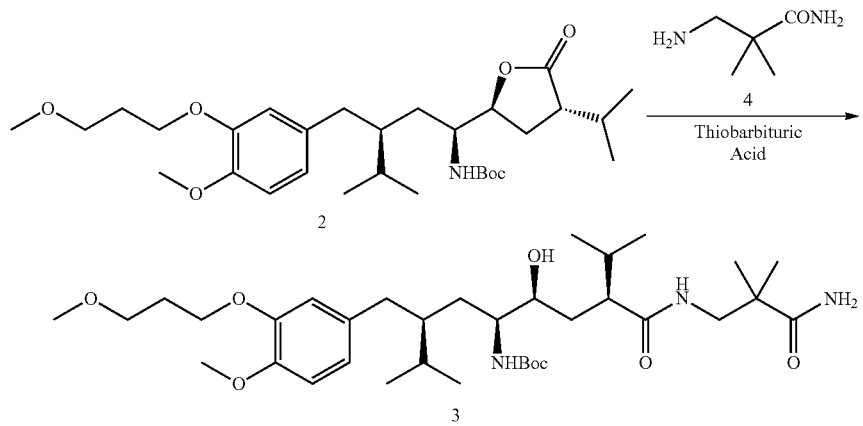

Thiobarbituric acid (0.07 g, 0.48 mmol) is added to a stirred suspension of the lactone(2) (0.58 g, 1.08 mmol) and the amine (4) (0.31 g, 2.67 mmol) in heptane (6.0 mL).

The mixture is warmed to 60° C. and maintained under magnetic stirring overnight.

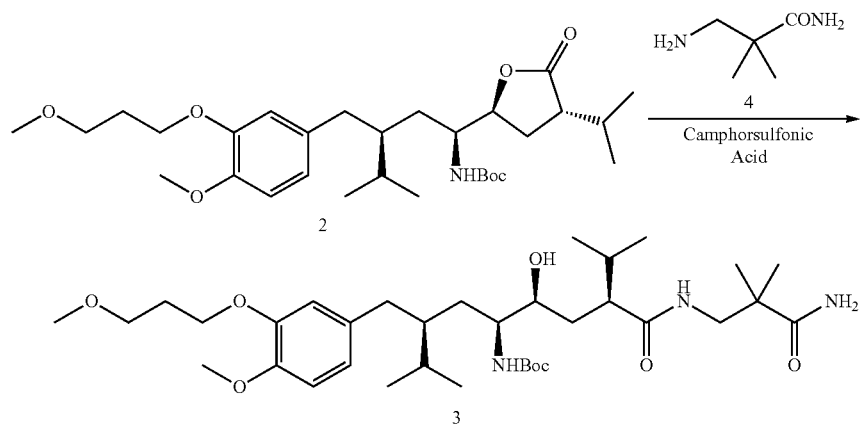

Camphorsulfonic acid (0.12 g, 0.52 mmol) is added to a stirred suspension of the lactone(2) (0.56 g, 1.04 mmol) and the amine (4) (0.30 g, 2.58 mmol) in heptane (5 mL).

The mixture is warmed to 60° C. and maintained under magnetic stirring overnight.

After cooling to room temperature water (20.0 mL) is added with stirring to obtain a suspension, which could be easily filtered, and then washed with water and heptane.

A mixture (2):(3)=75:25 is obtained in the solid.

Example 8

Preparation of benzyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHCbz, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (10.0 mL) is added with stirring to obtain a suspension, which can be easily filtered, and then washed with water and heptane.

The residue can be further purified crystallizing from isopropyl acetate obtaining (6) (0.65 g, 75%) as a white solid.

Example 9

Preparation of benzyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHCbz, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

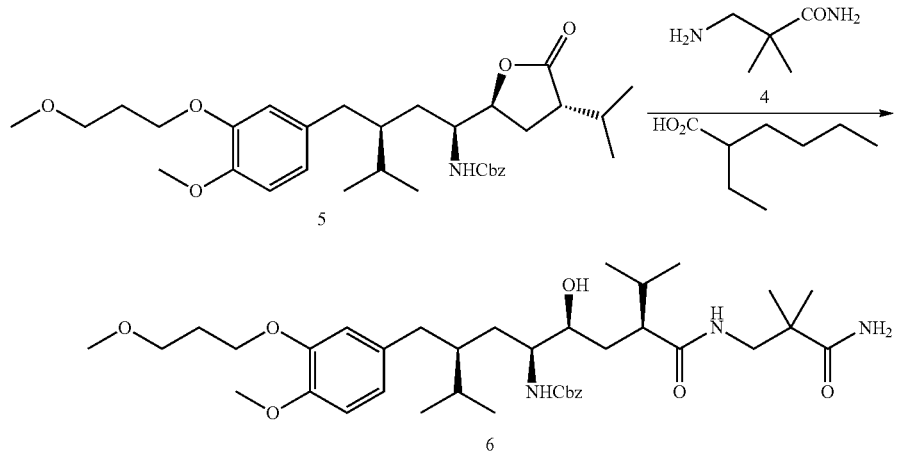

2-Ethylhexanoic acid (0.09 g, 0.62 mmol) is added to a stirred suspension of the lactone(5) (0.72 g, 1.26 mmol) and the amine (4) (0.37 g, 3.18 mmol) in heptane (8.0 mL).

The mixture is warmed to 60° C. and maintained under magnetic stirring until a conversion (by HPLC) higher than 80% is achieved.

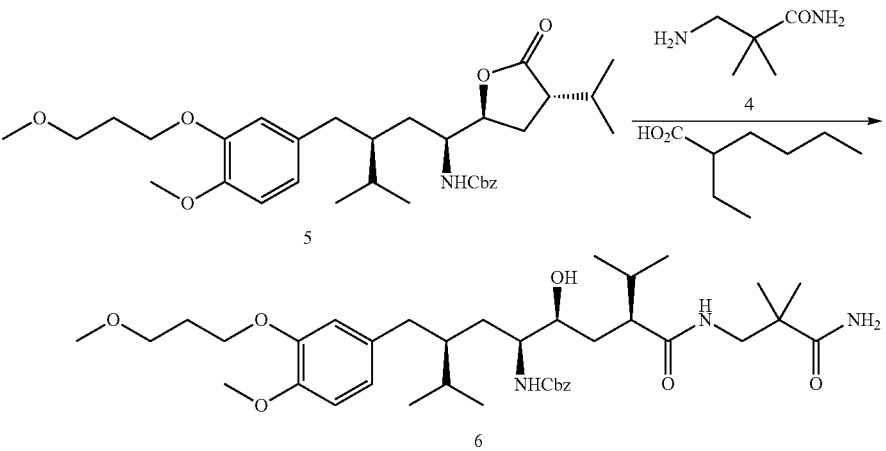

2-Ethylhexanoic acid (0.10 g, 0.69 mmol) is added to a stirred suspension of the lactone(5) (0.82 g, 1.44 mmol) and the amine (4) (0.42 g, 3.61 mmol) in cyclohexane (8.0 mL).

The mixture is warmed to 60° C. and maintained under magnetic stirring until a conversion (by HPLC) higher than 80% is achieved.

After cooling to room temperature water (8.0 mL) is added with stirring to obtain a suspension, which can be easily filtered, and then washed with water and cyclohexane.

The residue can be further purified crystallizing from isopropyl acetate obtaining (6) (0.74 g, 75%) as a white solid.

Example 10

Preparation of benzyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which R¹=OMe, R²=iPr, R³=NHCbz, R⁶=iPr, R⁴=0, R⁷=H, R⁸=H, R¹⁰=H, R⁹=O(CH₂)₃OCH₃, R=CH₂C(CH₃)₂CONH₂.

After cooling to room temperature water (8.0 mL) is added with stirring to obtain a suspension, which can be easily filtered, and then washed with water and isopropyl ether.

The residue can be further purified crystallizing from isopropyl acetate obtaining (6) (0.74 g, 86%) as a white solid.

Example 11

Preparation of benzyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which R¹=OMe, R²=iPr, R³=NHCbz, R⁶=iPr, R⁴=0, R⁷=H, R⁸=H, R¹⁰=H, R⁹=O(CH₂)₃OCH₃, R=CH₂C(CH₃)₂CONH₂.

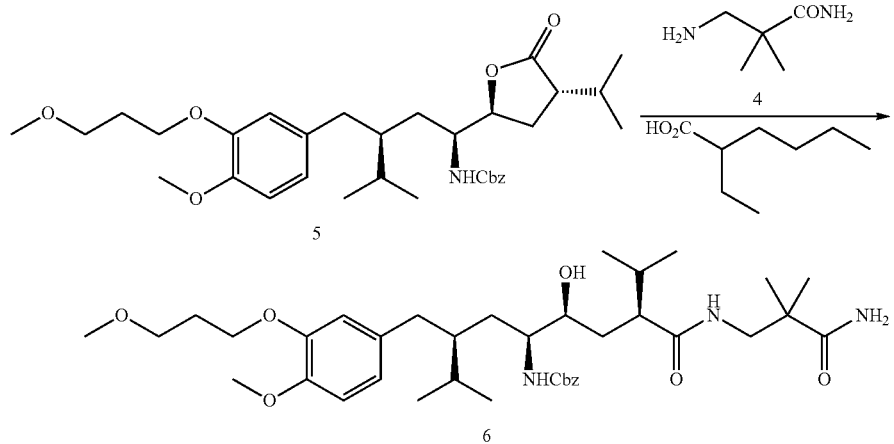

2-Ethylhexanoic acid (0.09 g, 0.69 mmol) is added to a stirred suspension of the lactone(5) (0.71 g, 1.25 mmol) and the amine (4) (0.36 g, 3.10 mmol) in isopropyl ether (7.0 mL).

The mixture is warmed to 60° C. and maintained under magnetic stirring until a conversion (by HPLC) higher than 90% is achieved.

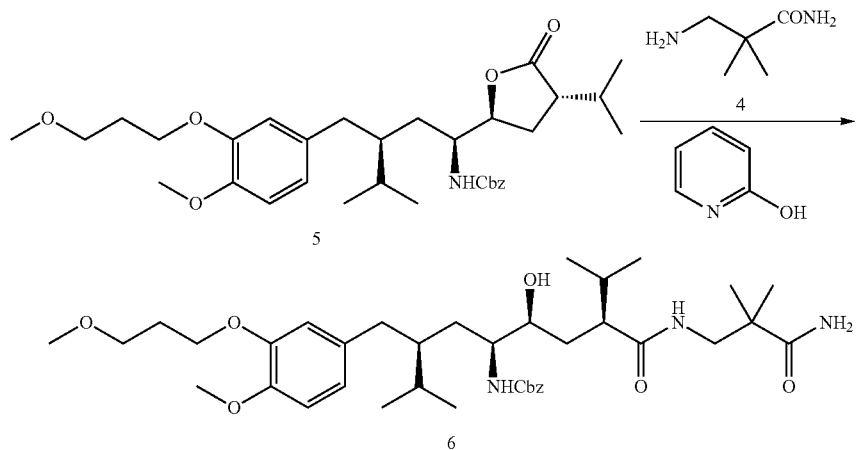

2-hydroxypiridine (0.14 g, 1.47 mmol) is added to a stirred suspension of the lactone(5) (0.82 g, 1.44 mmol) and the amine (4) (0.42 g, 3.61 mmol) in isopropyl ether (8.0 mL).

The mixture is warmed to 60° C. and maintained under magnetic stirring until a conversion (by HPLC) higher than 80% is achieved.

After cooling to room temperature water (8.0 mL) is added with stirring to obtain a suspension, which can be easily filtered, and then washed with water and isopropyl ether.

The residue can be further purified crystallizing from isopropyl acetate obtaining (6) (0.69 g, 70%) as a white solid.

Example 12

Preparation of (2S,4S,5S,7S)-5-amino-N-(3-amino-2,2-dimethyl-3-oxopropyl)-4-hydroxy-2-isopropyl-7-(4-methoxy-3-(3-methoxypropoxy)benzyl)-8-methylnonanamide hemifumarate salt, compound of formula (III) in which $R^1$=OMe, $R^2$=iPr, $R^3$=NH$_2$, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

When the reaction is complete, the mixture is poured in a cold (5-10° C.) aqueous solution of Na$_2$CO$_3$ and the two layers are separated. The organic phase is evaporated under vacuum to obtain Aliskiren (1) in quantitative yield. Fumaric acid (0.08 g, 0.69 mmol) is added to a stirred solution of the so obtained Aliskiren in EtOH (4.0 mL).

The solution is evaporated under vacuum maintaining the bath temperature under 30° C. The residue is crystallized from a mixture acetonitrile/ethanol 95:5 (10.0 mL). After drying at 60° C. Aliskiren Hemifumarate salt is obtained (0.87 g, 85%) in a HPLC purity ≥99.9%.

Example 13

Preparation of (2S,4S,5S,7S)-5-amino-N-(3-amino-2,2-dimethyl-3-oxopropyl)-4-hydroxy-2-isopropyl-7-(4-methoxy-3-(3-methoxypropoxy)benzyl)-8-methylnonanamide hemifumarate salt, compound of formula (III) in which $R^1$=OMe, $R^2$=iPr, $R^3$=NH$_2$, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

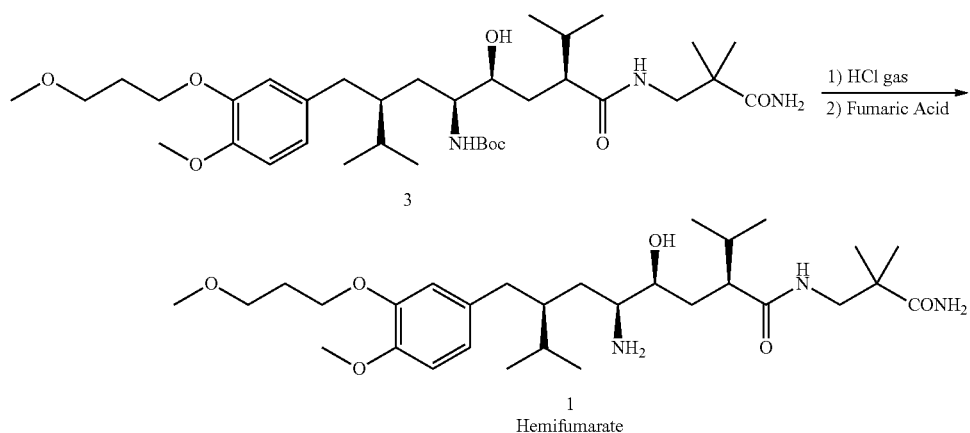

A stirred solution of N-Boc-Aliskiren (3) (1.00 g, 1.53 mmol) in dichloromethane (10.0 mL) at −10° C. is saturated with HCl gas and maintained under magnetic stirring for 3 hours at 0° C. monitoring by HPLC.

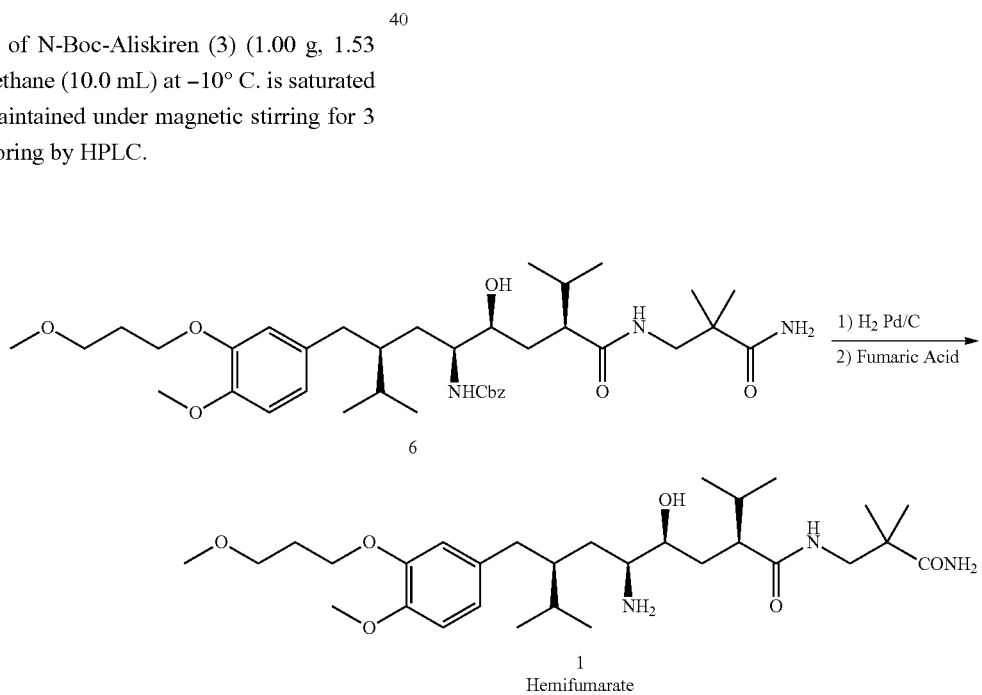

Pd/C 10%, 50% wet w/w (0.06 g, 0.03 mmol) is added to a stirred solution of N-Cbz-Aliskiren (6) (0.77 g, 1.12 mmol) in isopropanol (7.0 mL). The mixture is hydrogenated at atmospheric pressure and at room temperature up to complete conversion by HPLC.

The catalyst is filtered and the solution is evaporated under vacuum maintaining the bath temperature under 30° C. to obtain Aliskiren (1) in quantitative yield.

Fumaric acid (0.08 g, 0.69 mmol) is added to a stirred solution of the so obtained Aliskiren in EtOH (3.0 mL).

The solution is evaporated under vacuum maintaining the temperature bath under 30° C. The residue is crystallized from a mixture acetonitrile/ethanol 95:5 (8.0 mL). After drying at 60° C. Aliskiren hemifumarate salt is obtained (0.77 g, quantitative yield) in a HPLC purity ≥99.9%.

Example 14

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

The mixture is warmed to 60° C. and maintained under magnetic stirring until a conversion of 98% by HPLC quantitative assay is achieved (reaction time about 50 hours).

After cooling to room temperature water (10 mL) is added with stirring to obtain a suspension, which can be easily filtered, and then washed with water and hexane.

Example 15

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

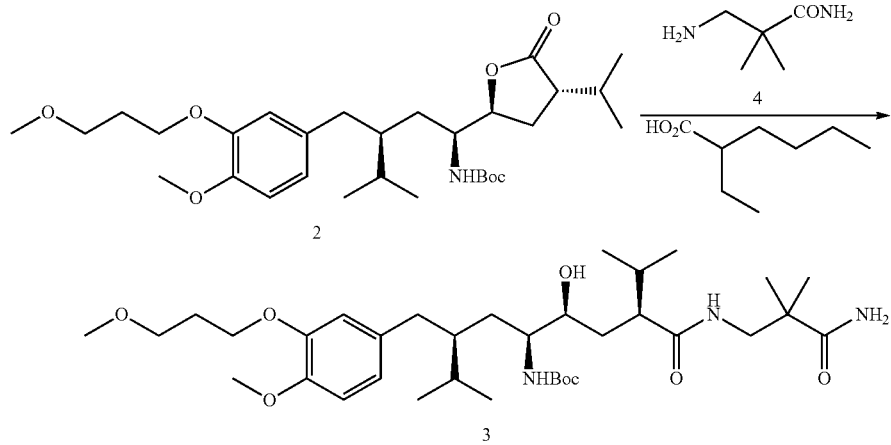

2-Ethylhexanoic acid (0.13 g, 0.90 mmol) is added to a stirred suspension of the lactone (2) (0.95 g, 1.77 mmol) and the amine (4) (0.52 g, 4.47 mmol) in hexane (10 mL).

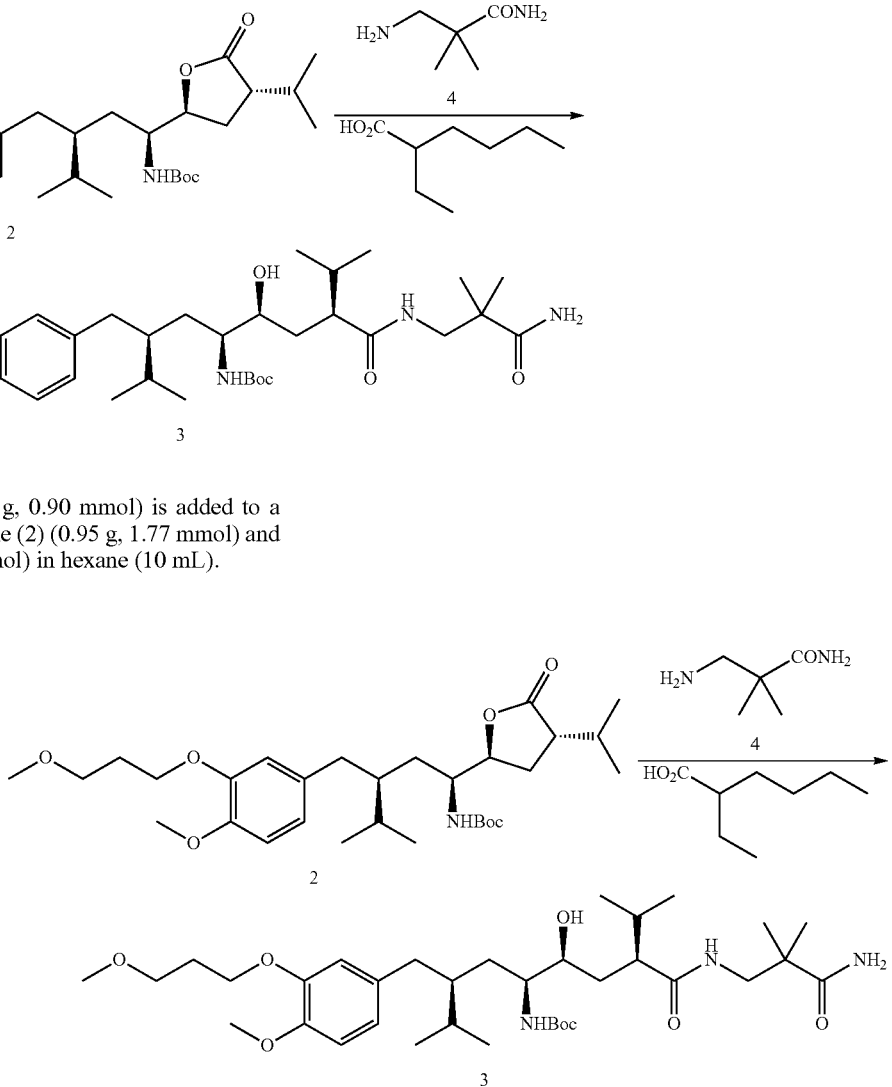

2-Ethylhexanoic acid (0.13 g, 0.90 mmol) is added to a stirred suspension of the lactone (2) (0.95 g, 1.77 mmol) and the amine (4) (0.52 g, 4.47 mmol) in octane (10 mL).

The mixture is warmed to 60° C. and maintained under magnetic stirring until a conversion of 94% by HPLC quantitative assay is achieved (reaction time about 50 hours).

After cooling to room temperature water (10 mL) is added with stirring to obtain a suspension, which can be easily filtered, and then washed with water and octane.

Example 16

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (10 mL) is added with stirring to obtain a suspension, which can be easily filtered, and then washed with water and isooctane.

Example 17

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

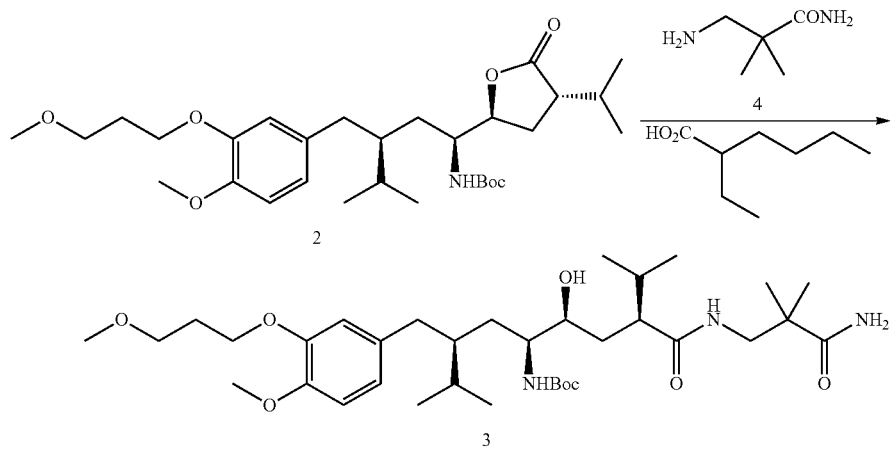

2-Ethylhexanoic acid (0.13 g, 0.90 mmol) is added to a stirred suspension of the lactone (2) (0.95 g, 1.77 mmol) and the amine (4) (0.52 g, 4.47 mmol) in isooctane (10 mL).

The mixture is warmed to 60° C. and maintained under magnetic stirring until a conversion of 93% by HPLC quantitative assay is achieved (reaction time about 50 hours).

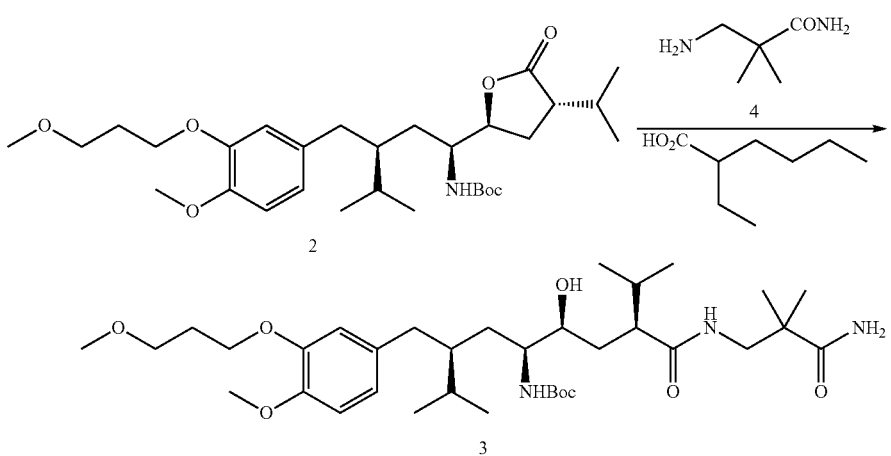

2-Ethylhexanoic acid (0.13 g, 0.90 mmol) is added to a stirred suspension of the lactone (2) (0.95 g, 1.77 mmol) and the amine (4) (0.52 g, 4.47 mmol) in methyl-tert-butyl ether (10 mL).

The mixture is warmed to 50° C. and maintained under magnetic stirring until a conversion of 90% by HPLC quantitative assay is achieved (reaction time about 70 hours).

After cooling to room temperature water (10 mL) is added with stirring to obtain a suspension, which can be easily filtered, and then washed with water and methyl-tert-butyl ether.

Example 18

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

After cooling to room temperature water (10 mL) is added with stirring to obtain a suspension, which can be easily filtered, and then washed with water and dibutyl ether.

Example 19

Comparative

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

This example is carried out using toluene as the solvent for the process of the present invention; toluene is described as a suitable solvent for the opening of lactone or lactam ring-containing compounds in international patent application WO 2011/019789. The reaction condition are summarized below:

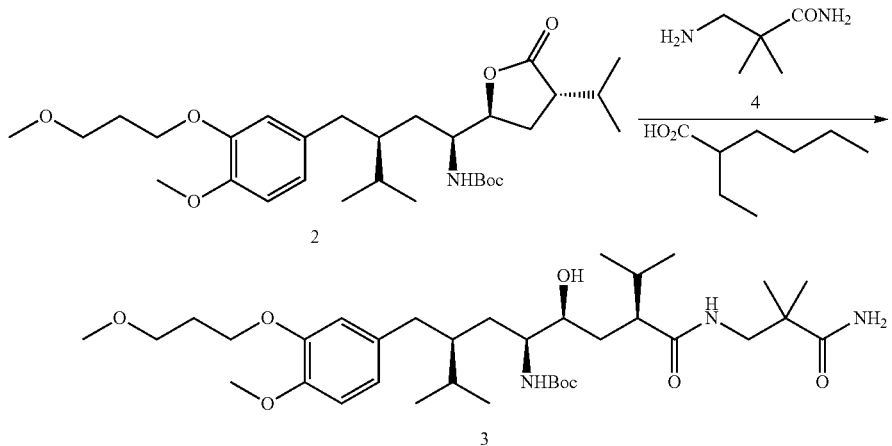

2-Ethylhexanoic acid (0.13 g, 0.90 mmol) is added to a stirred suspension of the lactone (2) (0.95 g, 1.77 mmol) and the amine (4) (0.52 g, 4.47 mmol) in dibutyl ether (10 mL).

The mixture is warmed to 60° C. and maintained under magnetic stirring until a conversion of 95% by HPLC quantitative assay is achieved (reaction time about 70 hours).

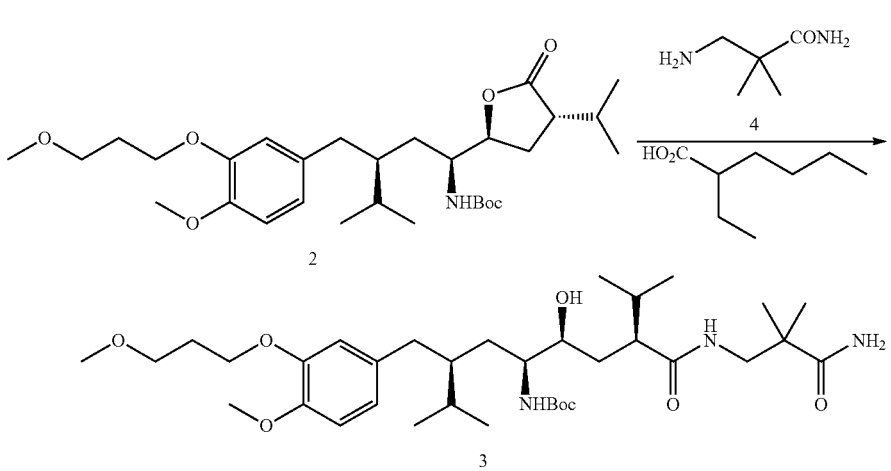

2-Ethylhexanoic acid (0.13 g, 0.90 mmol) is added to a stirred suspension of the lactone (2) (0.95 g, 1.77 mmol) and the amine (4) (0.52 g, 4.47 mmol) in toluene (10 mL).

The solution is warmed to 60° C. and maintained under magnetic stirring for 60 hours. The conversion measured by HPLC quantitative assay is 65%.

Example 20

Comparative

Preparation of tert-butyl ((3S,5S,6S,8S)-8-((3-amino-2,2-dimethyl-3-oxopropyl)carbamoyl)-6-hydroxy-3-(4-methoxy-3-(3-methoxypropoxy)benzyl)-2,9-dimethyldecan-5-yl)carbamate, compound of formula (III) in which $R^1$=OMe, $R^2$=iPr, $R^3$=NHBoc, $R^6$=iPr, $R^4$=O, $R^7$=H, $R^8$=H, $R^{10}$=H, $R^9$=O(CH$_2$)$_3$OCH$_3$, R=CH$_2$C(CH$_3$)$_2$CONH$_2$.

This example has been carried out in xylene, a solvent with similar properties with respect to toluene used in comparative example 19. The reaction condition are summarized below:

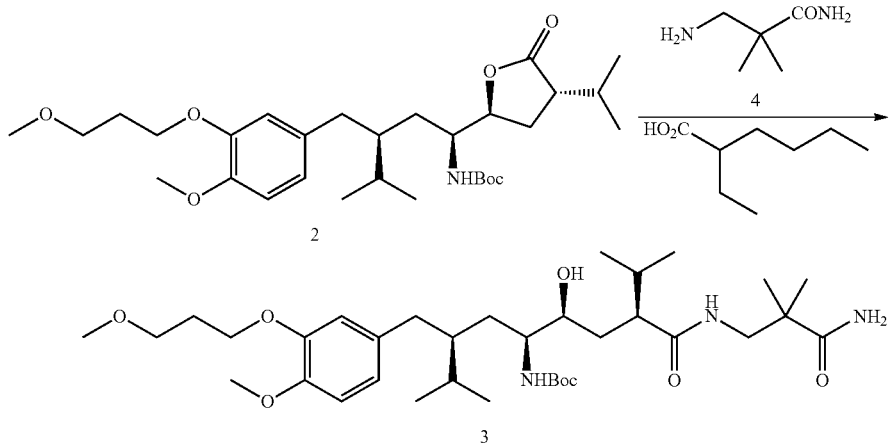

2-Ethylhexanoic acid (0.13 g, 0.90 mmol) is added to a stirred suspension of the lactone (2) (0.95 g, 1.77 mmol) and the amine (4) (0.52 g, 4.47 mmol) in xylene (10 mL).

The solution is warmed to 60° C. and maintained under magnetic stirring for 60 hours. The conversion measured by HPLC quantitative assay is 68%.

Comment to the Results

As can be derived from the examples of the invention and comparative examples above, one of the main features of the process of the present invention is that the solvent must be chosen so that the lactone or the lactam ring-containing compound is soluble in said solvent, and the amide obtained in the reaction is insoluble in the same solvent, under the reaction conditions. Examples 1-18 realize this condition, and confirm that operating according to the invention very good yields of the desired product can be obtained. To the contrary, comparative examples 19 and 20 show that operating, respectively, with toluene (the only solvent actually disclosed in WO 2011/019789) or the analogous solvent xylene, the yields are much worse. As shown in comparative examples 19 and 20, using as the solvent either toluene or xylene, at the reaction temperature (60° C.) the mixture is a clear solution and even upon cooling (down to 0° C.) of the mixture and upon seeding it with the product (3), no precipitation can be observed.

The invention claimed is:

1. An aminolysis process for the opening of a lactone or lactam ring, comprising the treatment of a compound containing said lactone or lactam ring with a primary or secondary amine in the presence of:
 a catalyst and optionally of a cocatalyst, in an aprotic apolar solvent selected from the group consisting of C5-C10 linear or branched alkanes, C5-C10 cycloalkanes, C5-C10 branched cycloalkanes, and C5-C10 dialkyl linear or branched ethers in which the lactone or the lactam ring-containing compound is soluble and the amide produced in the reaction is insoluble in the reaction conditions,
 wherein said primary or secondary amine has a general formula RR$^{10}$NH, in which R and R$^{10}$ are, independently from each other, hydrogen or a group selected among a linear or branched C1-C6 alkyl, a linear or branched C1-C6 alkyl substituted with at least a substituent selected among a cyano group, a free carboxylic group, an ester, an amide, an aldehyde or an acetal, or an aryl (C1-C6) alkyl, with the condition that R and R$^{10}$ cannot be both hydrogen, and the amount of said amine is not higher than 3.5 equivalents compared to the molar quantity of the lactone or lactam ring-containing compound.

2. The aminolysis process according to claim 1, in which the compound containing said lactone or lactam ring is a compound of formula (II) and is converted into an amide of formula (III):

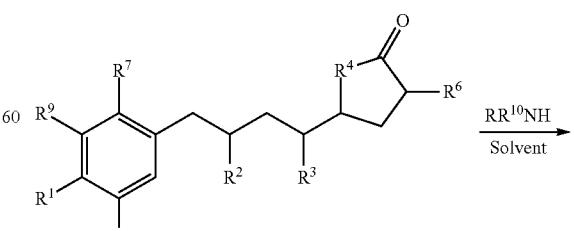

-continued

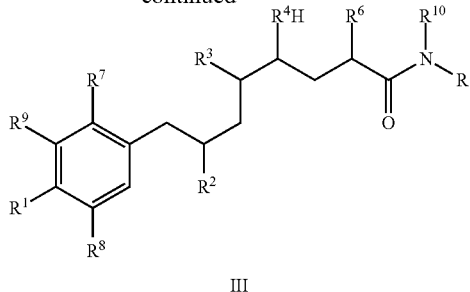

III in which the substituents have the following meanings;
wherein, $R^1$, $R^7$, $R^8$ and $R^9$ are, independently from each other, hydrogen, OH, OPg or a group selected among alkoxy C1-C10 or —$OR^5OR^{11}$,
wherein, $R^2$ is a group selected among a linear or branched C1-C6 alkyl or a linear or branched C1-C6 alkenyl,
wherein, $R^3$ is selected among $NH_2$, NHPg, $N(Pg)_2$, $N_3$, halogen, $NO_2$, OH, OLg,
wherein, $R^4$ is selected among O, NH, NPg,
wherein, $R^5$ is a group selected among a linear or branched C1-C6 alkyl or a linear or branched C1-C6 alkenyl,
wherein, $R^6$ is a group selected among a linear or branched C1-C6 alkyl or a linear or branched C1-C6 alkenyl,
wherein, $R^{11}$ is a group selected among a linear or branched C1-C6 alkyl or a linear or branched C1-C6 alkenyl,
wherein, Pg is a protecting group of the hydroxy function or of the amine function, and
wherein, Lg is a leaving group.

3. The aminolysis process according to claim 1, in which the amount of amine RR10NH is not lower than 1.5 equivalents compared to the molar quantity of the lactone or lactam ring-containing compound (II).

4. The aminolysis process according to claim 1, in which said catalyst is a Brønsted acid.

5. The aminolysis process according to claim 4, in which said acid is a carboxylic acid.

6. The aminolysis process according to claim 5, in which said carboxylic acid is of the general formula $R^{12}CO_2H$ in which said group $R^{12}$ is a linear or branched alkyl, a cycloalkyl, a linear or branched alkenyl, an aryl, or an arylalkyl.

7. The aminolysis process according to claim 1, in which said catalyst is an aromatic heterocyclic compound containing a hydroxyl function (OH) optionally in equilibrium with its keto form.

8. The aminolysis process according to claim 1, in which said catalyst is selected between 2-ethylhexanoic acid and 2-hydroxypyridine.

9. The aminolysis process according to claim 3, in which the amount of amine $RR^{10}NH$ is comprised in a range between 2 and 3 equivalents compared to the molar quantity of lactone or lactam ring-containing compound (II).

10. The aminolysis process according to claim 1, in which the amount of catalyst used in the reaction is comprised between 0.5 and 1.5 equivalents compared to the molar quantity of lactone or lactam ring-containing compound (II).

11. The aminolysis process according to claim 7 in which is used as cocatalyst a tertiary amine, in which the substituents linked to the nitrogen atom are selected among a linear or branched C1-C7 alkyl, a linear or branched C1-C7 alkenyl, a C3-C8 cycloalkyl, an aryl, an arylalkyl, a heteroaryl, a heteroarylalkyl.

12. The aminolysis process according to claim 11, in which said cocatalyst is selected among triethylamine, 1,8-Diazabicyclo[5.4.0]undec-7-ene (DBU), ethyldiisopropylamine, pyridine, N-methylmorpholine and 4-dimethylaminopyridine (DMAP).

13. The aminolysis process according to claim 11, in which the cocatalyst is used in an amount comprised between 0.5 and 1.5 equivalents compared to the molar quantity of lactone or lactam ring-containing compound (II).

14. The aminolysis process according to claim 1, in which said solvent is selected among heptane, isopropyl ether, and cyclohexane.

15. The aminolysis process according to claim 1, in which the $RR^{10}NH$ amine is 3-amino-2,2-dimethylpropanamide.

16. The aminolysis process according to claim 2, wherein tert-butyl ((1S,3S)-1-((2S,4S)-4-isopropyl-5-oxotetrahydrofuran-2-yl)-3-(4-methoxy-3-(3-methoxypropoxyl)benzyl)-4-methylpentyl)carbamate, a compound of formula (II) in which is $R^1$=OMe, $R^2$=iPr, $R^3$=NHBoc, $R^4$=O, $R^6$=iPr, $R^7$=$R^8$=H and $R^9$=O(CH$_2$)$_3$OCH$_3$ is transformed into ((3S, 5S,6S,8S)-8-((3-amino-2,2-dimethyl-3-oxopropyl)carbamoyl)-6-hydroxy-3-(4-methoxy-3-(3-methoxypropoxy)-benzyl)-2,9-dimethyldecan-5-yl)carbamate, according to the reaction:

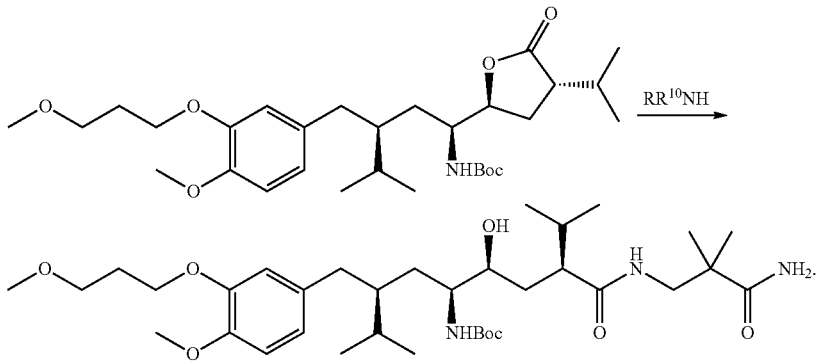

17. The aminolysis process according to claim 16, in which ((3S,5S,6S,8S)-8-((3-amino-2,2-dimethyl-3-oxopropyl)carbamoyl)-6-hydroxy-3-(4-methoxy-3-(3-methoxypropoxy)-benzyl)-2,9-dimethyldecan-5-yl)carbamate thus obtained is deprotected through removal of protecting group Boc, yielding the compound Aliskiren.

18. The aminolysis process according to claim 2, wherein benzyl-((1S,3S)-1-((2S,4S)-4-isopropyl-5-oxotetrahydrofuran-2-yl)-3-(4-methoxy-3-(3-methoxypropoxyl)benzyl)-4-methylpentyl)carbamate, a compound of formula (II) in which is $R^1$=OMe, $R^2$=iPr, $R^3$=NHCbz, $R^4$=O, $R^6$=iPr, $R^7$=$R^8$=H and $R^9$=O(CH$_2$)$_3$OCH$_3$ is transformed into ((3S, 5S,6S,8S)-8-((3-amino-2,2-dimethyl-3-oxopropyl)carbamoyl)-6-hydroxy-3-(4-methoxy-3-(3-methoxypropoxy)-benzyl)-2,9-dimethyldecan-5-yl)carbamate, according to reaction:

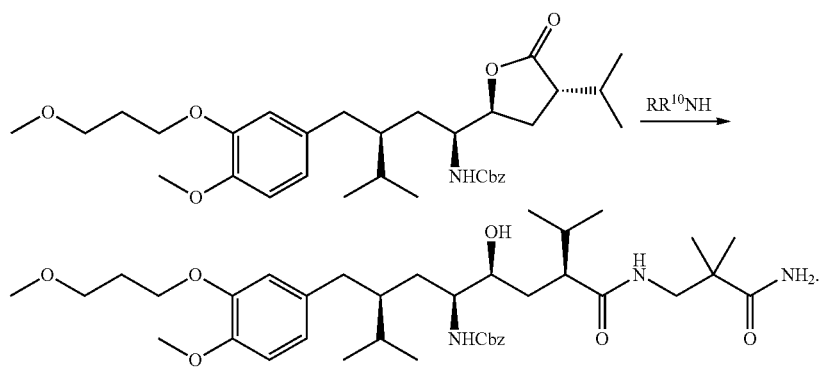
19. The aminolysis process according to claim 18, in which ((3S,5S,6S,8S)-8-((3-amino-2,2-dimethyl-3-oxopropyl)carbamoyl)-6-hydroxy-3-(4-methoxy-3-(3-methoxypropoxy)-benzyl)-2,9-dimethyldecan-5-yl)carbamate thus obtained is deprotected through removal of protecting group Cbz, yielding the compound Aliskiren.
\* \* \* \* \*